US012588856B2

(12) United States Patent
Shapira et al.

(10) Patent No.: US 12,588,856 B2
(45) Date of Patent: Mar. 31, 2026

(54) IDENTIFYING AND INDICATING CARDIAC AREAS EXHIBITING PROGRESSIVELY SLOWING ACTIVATION (PSA)

(71) Applicant: BIOSENSE WEBSTER (ISRAEL) LTD., Yokneam (IL)

(72) Inventors: Einat Shapira, Haifa (IL); Amir Ben-Dor, Haifa (IL); Gal Hayam, Tivon (IL); Tal Haim Bar-On, Kiryat Tivon (IL); Meir Bar-Tal, Haifa (IL); Kumaraswamy Nanthakumar, Mississauga (CA); Ahmed Niri, Toronto (CA); Stephane Masse, Toronto (CA)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 660 days.

(21) Appl. No.: 18/080,875

(22) Filed: Dec. 14, 2022

(65) Prior Publication Data

US 2024/0197233 A1    Jun. 20, 2024

(51) Int. Cl.
| | |
|---|---|
| *A61B 5/367* | (2021.01) |
| *A61B 5/287* | (2021.01) |
| *A61B 5/339* | (2021.01) |
| *A61B 5/364* | (2021.01) |

(52) U.S. Cl.
CPC .............. *A61B 5/364* (2021.01); *A61B 5/287* (2021.01); *A61B 5/339* (2021.01); *A61B 5/367* (2021.01)

(58) Field of Classification Search
CPC ................................. A61B 5/367; A61B 5/364
See application file for complete search history.

(56) References Cited

U.S. PATENT DOCUMENTS

| | | | |
|---|---|---|---|
| 5,391,199 | A | 2/1995 | Ben-Haim |
| 5,443,489 | A | 8/1995 | Ben Haim |
| 5,558,091 | A | 9/1996 | Acker |
| 5,954,661 | A | 9/1999 | Greenspon |
| 6,172,499 | B1 | 1/2001 | Ashe |
| 6,239,724 | B1 | 5/2001 | Doron |
| 6,332,089 | B1 | 12/2001 | Acker |

(Continued)

FOREIGN PATENT DOCUMENTS

WO    WO2020214439 A1    10/2020

OTHER PUBLICATIONS

International Search Report for corresponding PCT Appln. No. PCT/IB2023/061775 dated Apr. 8, 2024.

(Continued)

*Primary Examiner* — George R Evanisko
(74) *Attorney, Agent, or Firm* — Clayton, McKay & Bailey, PC

(57) ABSTRACT

A method includes receiving a cardiac signal that is sensed by electrodes at a location in a heart of a patient, the cardiac signal including signal components evoked by respective activations. The signal components in the cardiac signal are found and annotated. Respective time differences are calculated between the annotations and the corresponding activations. Based on the time differences, one or more cardiac tissue locations are identified, that demonstrate progressively slowing activation (PSA). An EP map of at least a portion of the heart is presented to a user, including providing a graphical indication of the one or more tissue locations that demonstrate the PSA.

14 Claims, 3 Drawing Sheets

(56)    References Cited

U.S. PATENT DOCUMENTS

| 6,484,118 | B1 | 11/2002 | Govari |
| 6,618,612 | B1 | 9/2003 | Acker |
| 6,690,963 | B2 | 2/2004 | Ben Haim |
| 6,788,967 | B2 | 9/2004 | Ben Haim |
| 6,892,091 | B1 | 5/2005 | Ben Haim |
| 7,536,218 | B2 | 5/2009 | Govari |
| 7,756,576 | B2 | 7/2010 | Levin |
| 7,848,787 | B2 | 12/2010 | Osadchy |
| 7,869,865 | B2 | 1/2011 | Govari |
| 8,456,182 | B2 | 6/2013 | Bar-Tal |
| 9,662,178 | B2 | 5/2017 | Nanthakumar |
| 10,729,345 | B2 | 8/2020 | Lou |
| 2022/0338784 | A1 * | 10/2022 | Hoyland ............... A61B 5/367 |

OTHER PUBLICATIONS

Furushima Hiroshi et al: "Significance of early onset and progressive increase of activation delay during premature stimulation in Brugada syndrome", Circulation, vol. 73, Jun. 17, 2009 (Jun. 17, 2009), pp. 1408-1415.
Bogossian Harilaos et al: "Visualization of local abnormal ventricular activities in scar-related ventricular tachycardia", Herzschrittmachertherapie Und Elektrophysiologie, Steinkopff, Darmstadt, DE, vol. 26, No. 1, Feb. 3, 2015 (Feb. 3, 2015), pp. 52-53.

* cited by examiner

Apply sequence of pacing pulses ~302

Receive pacing signal and chamber bipolar signal ~304

Annotate potentials evoked by pacing pulses ~306

Calculate time differences ~308

Identify chamber locations demonstrating PSA ~310

Indicate the PSA locations on an EP map ~312

IDENTIFYING AND INDICATING CARDIAC AREAS EXHIBITING PROGRESSIVELY SLOWING ACTIVATION (PSA)

FIELD OF THE DISCLOSURE

This disclosure relates generally to electrophysiological (EP) signals, and specifically to evaluation of electrical propagation in the heart.

BACKGROUND OF THE DISCLOSURE

Estimation of electrophysiological signals to determine local activation times (LATs) was previously suggested in the patent literature. For example, U.S. Pat. No. 5,954,661 describes heart tissue that is characterized by using pacing without inducing ventricular tachycardia (VT). With the tissue characterization, a patient's risk of developing VT can be determined and a slow conduction zone in the patient's heart can be determined. The characterization involves applying pacing signals with varying pacing cycle intervals to a chamber of the patient's heart to pace the patient's heart. The response signals generated by the paced heart are received and used as the basis for characterizing the patient's heart tissue.

The present disclosure will be more fully understood from the following detailed description of the examples thereof, taken together with the drawings, in which:

DETAILED DESCRIPTION OF EXAMPLES

Overview

Figure 1:
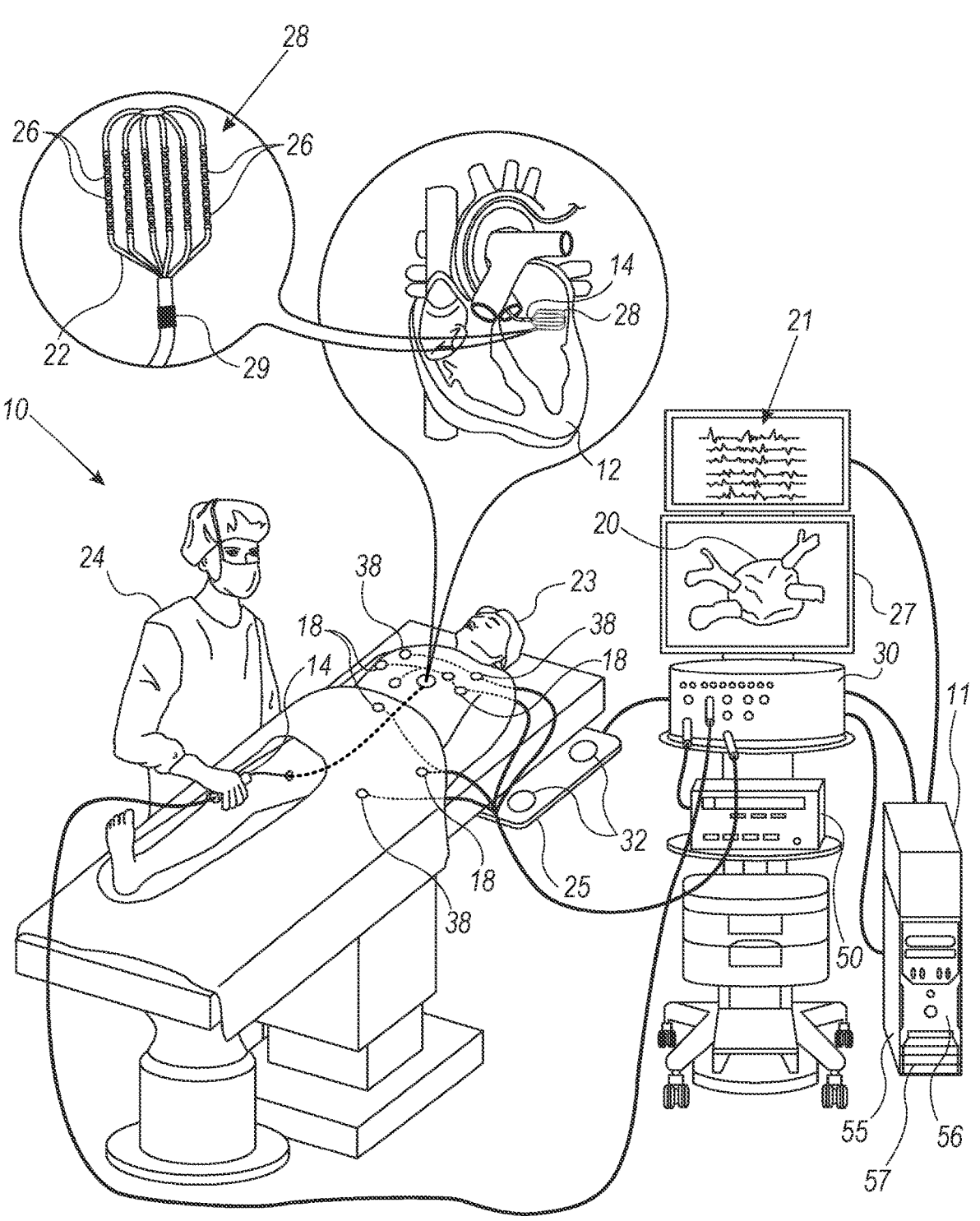
FIG. 1 is a schematic, pictorial illustration of a catheter-based electrophysiology (EP) mapping and ablation system, in accordance with an example of the present disclosure.

In order to characterize an arrhythmia (e.g., a reentry arrhythmia) of a cardiac chamber, a physician may use a multi-electrode mapping catheter to perform an electrophysiological (EP) mapping of suspected tissue pathways and circuits within the chamber.

In EP mapping, EP characteristics of the tissue, such as local activation times (LAT), are measured under sinus rhythm or under rapid pacing, and are then related to the arrhythmogenicity of the local tissue. A dedicated pacing catheter may be used to pace the cardiac chamber while an EP mapping catheter acquires bipolar electrograms from various tissue locations. A processor may run an algorithm that identifies tissue with unhealthy electrophysiological characteristics, such as locations demonstrating low bipolar potential and/or aberrant conduction times (relative to the timing of a pacing signal).

Once an arrhythmogenic tissue is identified, a dedicated ablative catheter may be used to eliminate a possibility of arrhythmia (e.g., by blocking a stray conduction path causing a reentry circuit by ablation).

In practice, however, it may be difficult to identify a unique EP pattern (e.g., temporal pattern) of an arrhythmogenic site or path due to, for example, inherent variability and signal noise.

The authors of this disclosure noted that, during pacing, the activation time measured in a remote tissue distance from the pacing site is sometimes progressively increased with the pacing cycles. This progressive increase, referred to hereinafter as Progressively Slowing Activation (PSA), typically indicates the presence of arrhythmogenic tissue (arrhythmogenicity may be either local or manifested as an arrhythmogenic tissue path between the pacing site and the measurement site). The abnormal tissue presence may be related to arrhythmogenicity of this tissue as part of a reentry type arrythmia.

Examples of the present disclosure that are described hereinafter provide PSA mapping methods and systems that automatically identify PSA behavior without inducing an actual arrhythmia. The methods and systems analyze, display, and notify a physician of the PSA behavior using visual, audial and/or tactile means. In one example, a processor displays the PSA behavior by overlaying a graphical indication of a cluster of PSA locations on a cardiac EP map.

The disclosed automated PSA mapping method includes receiving a pacing signal applied to a heart of a patient. The pacing signal comprises a sequence of regular pacing stimuli with a same cycle length (CL) between them, which is shorter than a naturally occurring sinus rhythm. (The CL can range between close to the normal sinus CL and much shorter than the CL). In the context of this description, the wording "regular pacing stimuli" covers pulses that are equidistant up to a predefined variation. Typically, the predefined variation is limited to an order of 1% of the specified equidistant interval, although larger deviations, e.g., 5%, can be tolerable in some cases. The pacing is typically applied by a dedicated pacing catheter in contact with cardiac tissue at a fixed location.

A responsive signal of a propagating cardiac activation wave is received, sensed by electrodes of a multi-electrode mapping catheter in contact with a tissue location in the heart. For each intra-cardiac bipolar channel of the multi-electrode mapping catheter, a processor finds and annotates the activation after each pace. A time difference (e.g., an LAT value) is calculated between each evoked potential and a fixed timing reference in the pacing pulse, e.g., the timing of the preceding pacing spike. This measurement of bipolar potential LAT is performed in a plurality of locations in the heart chamber.

A tissue location that exhibits an increasing time difference of at least two consecutive beats (i.e., over three consecutive pacing cycles) is identified as a possible PSA location.

The processor constructs and presents an EP map of at least a portion of the heart to a user, with a graphical indication of locations where the PSA behavior is found. Optionally, a boundary around a cluster of PSA sites is indicated. The physician may elect to ablate locations on the indicated boundary or the specific PSA sites.

Spatial stability of the catheter may also be monitored to ensure that there is no significant catheter movement that may cause changes in LAT between pacing cycles.

Finally, it is also possible (though less accurate) to identify PSA without pacing, using naturally occurring sinus rhythm activation.

Therefore, in one example, a system is provided, that includes an interface and a processor. The interface receives a cardiac signal that is sensed by electrodes at a location in a heart of a patient, the cardiac signal comprising signal components evoked by respective activations. The processor analyzes the evoked signal components so as to find and annotate the signal components in the cardiac signal. Then, the processor calculates respective time differences between the annotations and the corresponding activations. Based on the time differences, the processor identifies one or more cardiac tissue locations that demonstrate PSA. The processor presents an EP map of at least a portion of the heart to a user, including providing a graphical indication of the one or more tissue locations that demonstrate the PSA.

Typically, the processor is programmed in software containing a particular algorithm that enables the processor to conduct each of the processor-related steps and functions outlined above.

The disclosed technique of PSA mapping introduces a new and unique EP mapping tool to an arsenal of existing EP mapping tools, which may increase the sensitivity and specificity of EP mapping.

System Description

FIG. 1 is a schematic, pictorial illustration of a catheter-based electrophysiology (EP) mapping and ablation system 10, in accordance with an example of the present disclosure.

System 10 includes multiple catheters which are percutaneously inserted by physician 24 through the patient's vascular system into a chamber or vascular structure of a heart 12. Typically, a delivery sheath catheter is inserted into a cardiac chamber, such as the left or right atrium near a desired location in heart 12. Thereafter, a plurality of catheters can be inserted into the delivery sheath catheter so as to arrive at the desired location. The plurality of catheters may include a catheter dedicated for pacing, a catheter for sensing intracardiac electrogram signals, and a catheter dedicated for ablating and/or a catheter dedicated for both EP mapping and ablating. An example catheter 14 that is configured for sensing bipolar electrograms is illustrated herein. Physician a distal tip 28 (also called hereinafter "distal-end assembly 28") of catheter 14 into contact with the heart wall for sensing a target site in heart 12. For ablation, physician 24 similarly brings a distal end of an ablation catheter to a target site for ablating.

Catheter 14 is an exemplary catheter that includes one, and preferably multiple, electrodes 26 optionally distributed over a plurality of splines 22 at distal tip 28 and configured to sense the IEGM signals. Catheter 14 may additionally include a position sensor 29 embedded in or near distal tip 28 for tracking position and orientation of distal tip 28. Optionally and preferably, position sensor 29 is a magnetic-based position sensor including three magnetic coils for sensing three-dimensional (3D) position and orientation.

Magnetic-based position sensor 29 may be operated together with a location pad 25 including a plurality of magnetic coils 32 configured to generate magnetic fields in a predefined working volume. Real-time position of distal tip 28 of catheter 14 may be tracked based on magnetic fields generated with location pad 25 and sensed by magnetic-based position sensor 29. Details of the magnetic based position sensing technology are described in U.S. Pat. Nos.

5,5391,199; 5,443,489; 5,558,091; 6,172,499; 6,239,724; 6,332,089; 6,484,118; 6,618,612; 6,690,963; 6,788,967; 6,892,091.

System 10 includes one or more electrode patches 38 positioned for skin contact on patient 23 to establish location reference for location pad 25 as well as impedance-based tracking of electrodes 26. For impedance-based tracking, electrical current is directed toward electrodes 26 and sensed at electrode skin patches 38 so that the location of each electrode can be triangulated via the electrode patches 38. Details of the impedance-based location tracking technology are described in U.S. Pat. Nos. 7,536,218; 7,756,576; 7,848, 787; 7,869,865; and 8,456,182.

A recorder 11 displays electrograms 21 captured with body surface ECG electrodes 18 and intracardiac electrograms captured with electrodes 26 of catheter 14. Recorder 11 may include pacing capability to pace the heart rhythm and/or may be electrically connected to a standalone pacer.

System 10 may include an ablation energy generator 50 that is adapted to conduct ablative energy to one or more electrodes at a distal tip of a catheter configured for ablating. Energy produced by ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

Patient interface unit (PIU) 30 is an interface configured to establish electrical communication between catheters, electrophysiological equipment, power supply and a workstation 55 to control system 10 operation. Electrophysiological equipment of system 10 may include, for example, multiple catheters, location pad 25, body surface ECG electrodes 18, electrode patches 38, ablation energy generator 50, and recorder 11. Optionally, and preferably, PIU 30 additionally includes processing capability for implementing real-time computations of catheter locations and for performing ECG calculations.

Workstation 55 includes memory 57, processor 56 unit with memory or storage with appropriate operating software loaded therein, and user interface capability. Workstation 55 may provide multiple functions, optionally including (1) modeling endocardial anatomy in three-dimensions (3D) and rendering the model or anatomical map 20 for display on a display device 27, (2) displaying on display device 27 activation sequences (or other data) compiled from recorded electrograms 21 in representative visual indicia or imagery superimposed on the rendered anatomical map 20, (3) displaying real-time location and orientation of multiple catheters within the heart chamber, and (5) displaying on display device 27 sites of interest such as places where ablation energy has been applied. One commercial product embodying elements of the system 10 is available as the CARTO™ 3 System, available from Biosense Webster, Inc., 31A Technology Drive, Irvine, CA 92618.

In some examples, processor 56 typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

This particular configuration of system 10 is shown by way of example, in order to illustrate certain problems that are addressed by examples of the present disclosure and to demonstrate the application of these examples in enhancing the performance of such a system. Examples of the present disclosure, however, are by no means limited to this specific sort of example system, and the principles described herein may similarly be applied to other sorts of medical systems. For example, other types of multi-electrode catheter may be used, such as the OCTARAY™ catheter or a basket catheter.

Identifying Locations Exhibiting PSA

Figure 2:
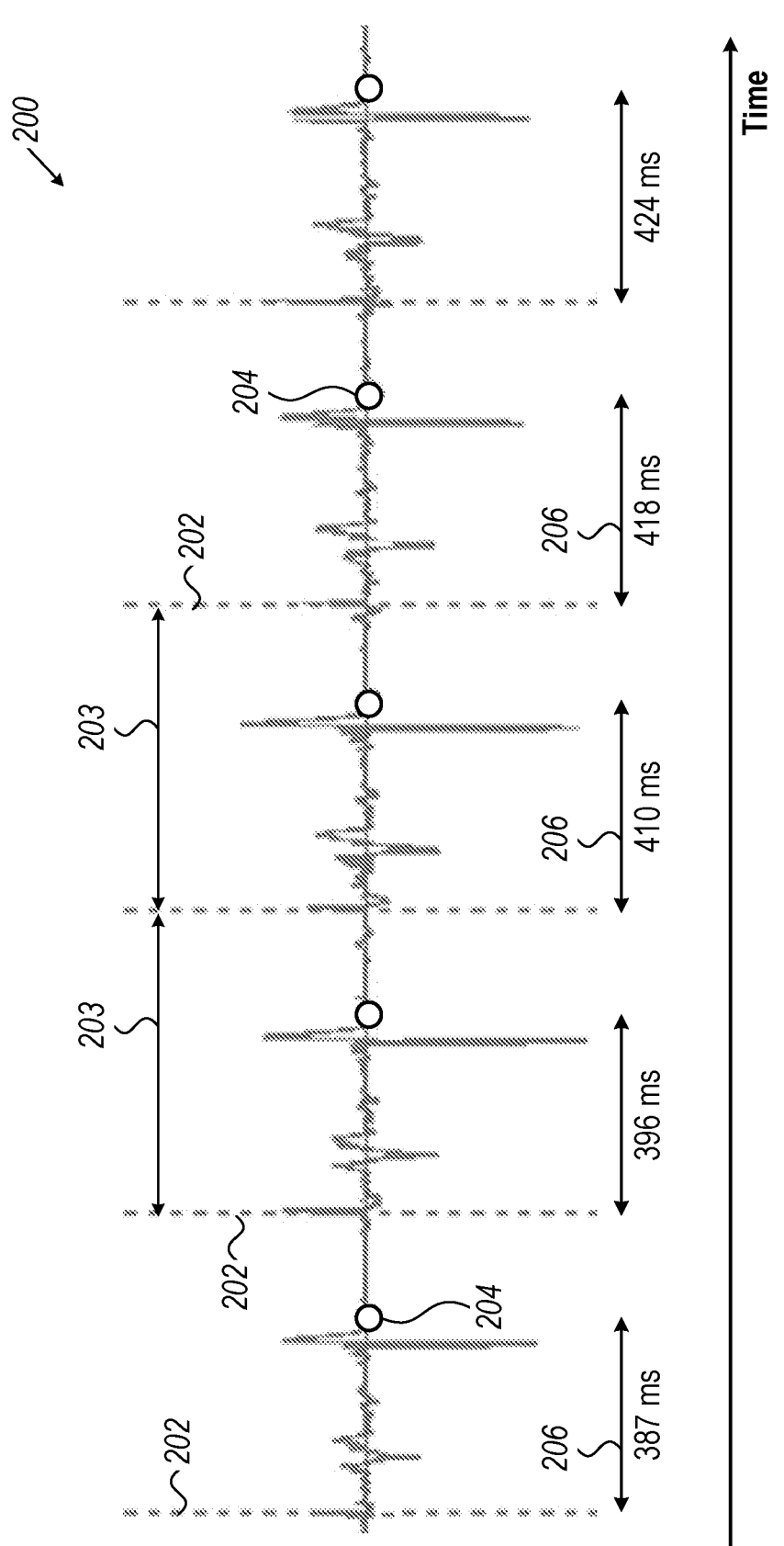
FIG. 2 shows an example graph of a bipolar electrogram acquired using the system of FIG. 1, with progressively slowing activation (PSA) potentials annotated on the bipolar signal, according to an example of the present disclosure.

FIG. 2 shows an example graph of a bipolar electrogram 200 acquired using system 10 of FIG. 1, with PSA potentials annotated (204) on the bipolar signal, according to an example of the present disclosure. The dashed lines 202 indicate timing of equidistant (203) pacing stimuli (e.g., the aforementioned respective activations).

As seen, over the five pacing cycles, annotations 204 made by the processor to evoked signal components occur as five consecutive PSA time differences 206 of 387, 396, 410, 418, and 424 milliseconds. The processor then calculates a respective sequence of changes in time differences. For the electrogram in FIG. 2, this amounts to a sequence of four increments due to PSA with values +9, +14, +8, and +6 milliseconds. As found by the authors, such consistent PSA behavior is highly predictable that the location at which electrogram 200 was acquired is an arrhythmogenic region.

FIG. 2 is brought by way of example, and the method can be applied with different types of electrograms. In particular the method can have the PSA annotated on unipolar or multipolar electrograms.

Method of Identifying and Indicating Areas Exhibiting PSA

Figure 3:
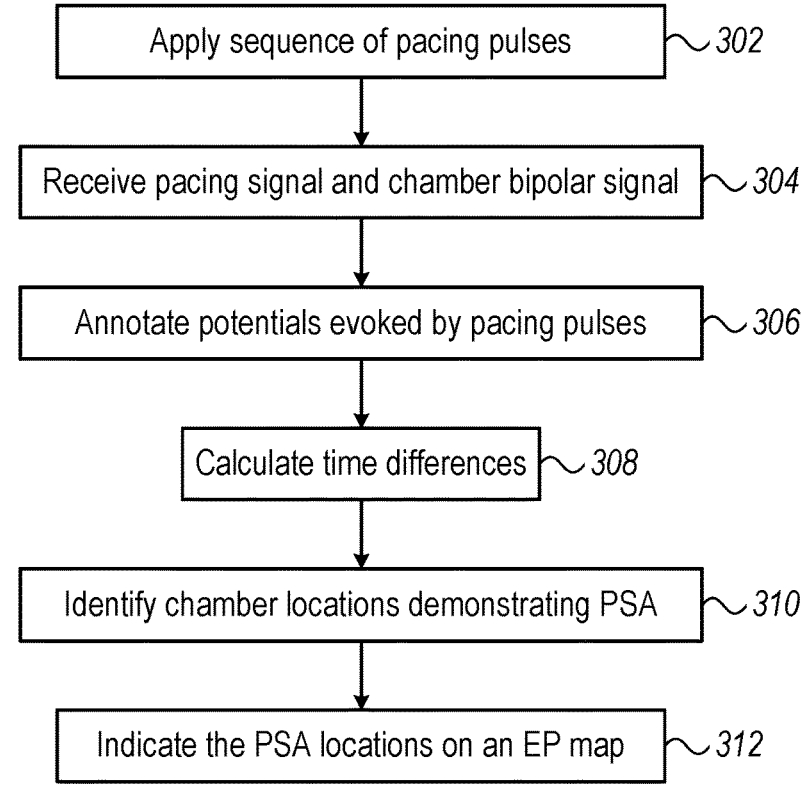
FIG. 3 is a flow chart that schematically illustrates a method and algorithm for finding cardiac chamber tissue locations that demonstrate PSA, according to an example of the present disclosure.

FIG. 3 is a flow chart that schematically illustrates a method and algorithm for finding cardiac chamber tissue locations that demonstrate PSA, according to an example of the present disclosure. The algorithm, according to the presented example, carries out a process that begins with system 10 applying a pacing signal as a form of a sequence of equidistant (203) pacing pulses, at a pacing step 302.

At EP data receiving step 304, processor 56 receives the pacing signal, the bipolar signal (e.g., waveform) from catheter 14, and respective ECG signal from a body surface (BS) electrode.

Next, at EP response extraction step 306, processor 56 annotates (204) the evoked potentials. The processor may use an annotation algorithm made by Biosense Webster to identify late potentials.

Using pacing stimuli timings 202, and annotations 204 made by the processor, processor 56 calculates time differences 206, at time difference calculation step 308.

At PSA analysis step 310, processor 56 calculates a respective sequence of changes in time differences 206, such as done in FIG. 2, and uses criteria to identify chamber locations that demonstrate PSA. One example of a criterion is that a tissue location exhibits an increasing time difference of at least two consecutive beats (i.e., over three consecutive pacing cycles) to be identified as a possible PSA location.

Figure 4:
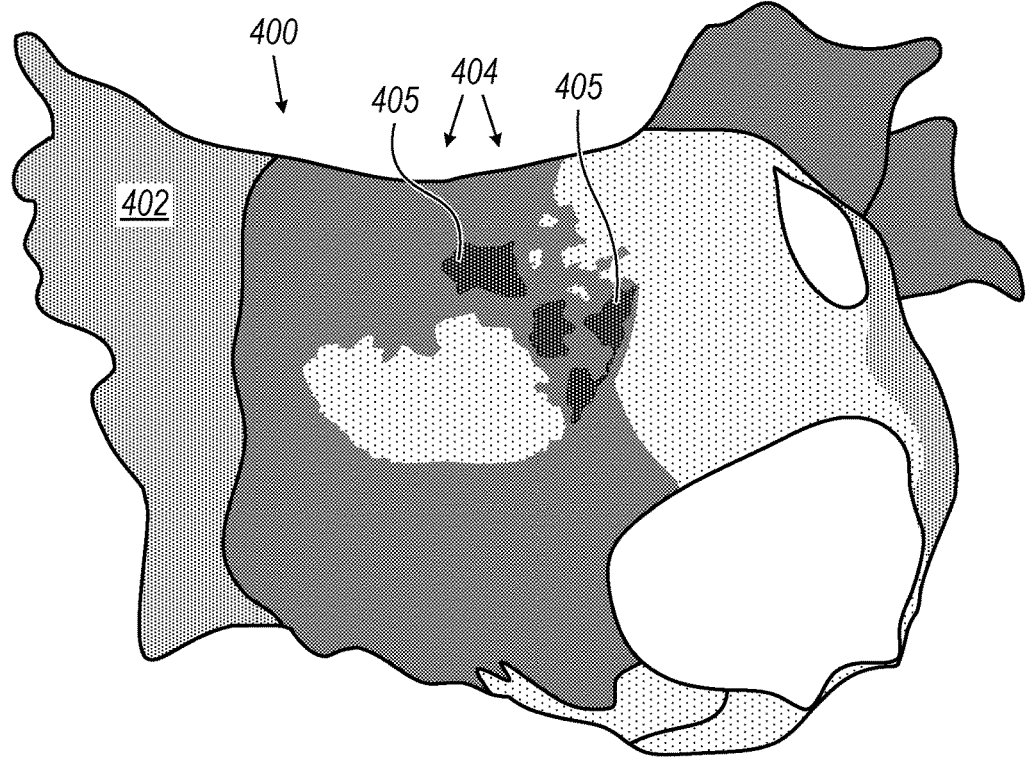
FIG. 4 is a schematic, pictorial volume rendering of an EP map that graphically indicates left atrium locations found to demonstrate PSA, in accordance with an example of the present disclosure.

Finally, processor 28 indicates the PSA locations on an EP map, as shown in FIG. 4 below, at PSA locations overlying step 312.

The example flow chart shown in FIG. 3 is chosen purely for the sake of conceptual clarity. The present example may also comprise additional steps of the algorithm, such as receiving multiple bipolar signals and ECG signals simultaneously, as well as receiving indications of the degree of physical contact of the electrodes with diagnosed tissue from a contact force sensor. This and other possible steps are omitted from the disclosure herein purposely in order to provide a more simplified flow chart.

PSA Map

FIG. 4 is a schematic, pictorial volume rendering of an EP map 400 that graphically indicates left atrium regions 404 found to demonstrate PSA, in accordance with an example of the present disclosure. EP map 400 shows an anatomical surface overlaid with a graphically encoded EP parameter 402, such as bipolar potential amplitude or LAT. Alternatively, FIG. 4 may show just the anatomical surface. In FIG. 4, dark regions 404 are encoded such to indicate one or more locations (e.g., a cluster of locations) identified by the disclosed technique to demonstrate PSA. As seen, processor 56 delineated a boundary 405 around each region 404 comprising a cluster of locations that demonstrate PSA. A physician may use delineations 405 to plan an ablation in order to eliminate an arrhythmia in that region.

If the PSA indication is overlayed on another EP layer, such as of the bipolar potential, the physician may assess a correlation between arrhythmogenic-indicative regions to refine the ablation plan. For example, regions that exhibit both PSA and low bipolar potentials may be considered scar regions to be homogenized so as to eliminate slow conduction paths therein.

EXAMPLES

Example 1

A method includes receiving a cardiac signal (21) that is sensed by electrodes (26) at a location in a heart (12) of a patient, the cardiac signal (21) comprising signal components evoked by respective activations. The signal components in the cardiac signal (21) are found and annotated (204). Respective time differences (206) are calculated between the annotations and the corresponding activations. Based on the time differences (206), one or more cardiac tissue locations are identified, that demonstrate progressively slowing activation (PSA). An EP map (400) of at least a portion of the heart (12) is presented to a user, including providing a graphical indication (405) of the one or more tissue locations that demonstrate the PSA.

Example 2

The method according to example 1, wherein the activations comprise pacing stimuli applied to the heart (12).

Example 3

The method according to any of examples 1 and 2, wherein the activations comprise naturally-occurring sinus rhythm activations of the heart (12).

Example 4

The method according to any of examples 1 through 3, wherein identifying the tissue locations that demonstrates the PSA comprises identifying one or more tissue locations that exhibit monotonically increasing time differences (206) over at least three consecutive cardiac cycles.

Example 5

The method according to any of examples 1 through 4, wherein providing the graphical indication (405) comprises delineating a boundary around a cluster of tissue locations that demonstrate the PSA.

Example 6

The method according to any of examples 1 through 5, wherein receiving the cardiac signal (21) comprises receiving unipolar and bipolar electrograms acquired using a catheter (14).

Example 7

The method according to any of examples 1 through 6, wherein annotating (204) the signal (21) components comprises annotating a bipolar electrogram, a unipolar electrogram, or a multipolar electrogram.

Example 8

A system includes an interface (30) an interface and a processor (56). The interface (30) is configured to receive a cardiac signal (21) that is sensed by electrodes (26) at a location in a heart (12) of a patient, the cardiac signal (21) comprising signal components evoked by respective activations. The processor (56) is configured to (i) find and annotate (204) the signal components in the cardiac signal (21), (ii) calculate respective time differences (206) between the annotations (204) and the corresponding activations, (iii) based on the time differences (206), identify one or more cardiac tissue locations that demonstrate progressively slowing activation (PSA), and (iv) present an EP map (400) of at least a portion of the heart (12) to a user, including providing a graphical indication (405) of the one or more tissue locations that demonstrate the PSA.

It will be appreciated that the examples described above are cited by way of example, and that the present disclosure is not limited to what has been particularly shown and described hereinabove. Rather, the scope of the present disclosure includes both combinations and subcombinations of the various features described hereinabove, as well as variations and modifications thereof which would occur to persons skilled in the art upon reading the foregoing description and which are not disclosed in the prior art.

The invention claimed is:

1. A method, comprising:

sensing a cardiac signal from electrodes at a location in a heart of a patient, the cardiac signal comprising signal components corresponding to respective activations;

finding and annotating the signal components in the cardiac signal;

calculating respective time differences between the annotations and the corresponding activations;

based on the time differences, identifying one or more cardiac tissue locations that demonstrate progressively slowing activation (PSA); and presenting an EP map of at least a portion of the heart to a user on a display, including providing a graphical indication of the one or more tissue locations that demonstrate the PSA.

2. The method according to claim 1, further comprising applying a pacing stimuli to the heart as the activations.

3. The method according to claim 1, wherein the activations comprise naturally-occurring sinus rhythm activations of the heart.

4. The method according to claim 1, wherein a cardiac cycle is defined as a period between successive activations, and wherein identifying the tissue locations that demonstrate the PSA comprises identifying one or more tissue locations that exhibit monotonically increasing time differences over at least three consecutive cardiac cycles.

5. The method according to claim 1, wherein providing the graphical indication comprises delineating a boundary around a cluster of tissue locations that demonstrate the PSA.

6. The method according to claim 1, wherein receiving the cardiac signal comprises receiving unipolar and bipolar electrograms from a catheter.

7. The method according to claim 1, wherein the cardiac signal is a bipolar electrogram, a unipolar electrogram, or a multipolar electrogram.

8. A system, including:

electrodes configured to sense a cardiac signal at a location in a heart of a patient, the cardiac signal comprising signal components corresponding to respective activations; a display; and a processor, which is configured to:

find and annotate the signal components in the cardiac signal;

calculate respective time differences between the annotations and the corresponding activations;

based on the time differences, identify one or more cardiac tissue locations that demonstrate progressively slowing activation (PSA); and present an EP map of at least a portion of the heart to a user for presentation at the display, the EP map including a graphical indication of the one or more tissue locations that demonstrate the PSA.

9. The system according to claim 8, wherein the electrodes are configured to apply pacing stimuli to the heart as the activations.

10. The system according to claim 8, wherein the activations comprise naturally-occurring sinus rhythm activations of the heart.

11. The system according to claim 8, wherein a cardiac cycle is defined as a period between successive activations, and wherein the processor is further configured to identify the tissue locations that demonstrate the PSA by identifying one or more tissue locations that exhibit monotonically increasing time differences over at least three consecutive cardiac cycles.

12. The system according to claim 8, wherein the processor is configured to provide the graphical indication by delineating a boundary around a cluster of tissue locations that demonstrate the PSA.

13. The system according to claim 8, further comprising a catheter including the electrodes, wherein the cardiac signal includes one or more unipolar or bipolar electrograms acquired from the catheter.

14. The system according to claim 8, wherein the cardiac signal is a bipolar electrogram, a unipolar electrogram, or a multipolar electrogram.

* * * * *